United States Patent [19]
Miyata et al.

[11] Patent Number: 4,748,152
[45] Date of Patent: May 31, 1988

[54] SUCCINYLATED ATELOCOLLAGEN SOLUTION FOR USE IN VISCOSURGERY AND AS A VITREOUS SUBSTITUTE

[75] Inventors: Teruo Miyata, Tokyo, Japan; Michael W. Dunn, New Rochelle, N.Y.

[73] Assignees: Opticol Corp., Stanford, Conn.; Koken Co., Ltd., Tokyo, Japan

[21] Appl. No.: 888,084

[22] Filed: Jul. 16, 1986

Related U.S. Application Data

[63] Continuation of Ser. No. 693,084, Jan. 22, 1985, abandoned.

[51] Int. Cl.[4] .................. A61K 37/12; C07K 15/20
[52] U.S. Cl. ........................... 514/2; 514/21; 514/801; 530/356; 424/427; 424/428; 424/429
[58] Field of Search .................. 424/427–429; 530/356; 514/2, 21, 801

[56] References Cited

U.S. PATENT DOCUMENTS

| 4,164,559 | 8/1979 | Miyata et al. | 424/14 |
| 4,223,984 | 9/1980 | Miyata et al. | 260/123.7 |
| 4,233,360 | 11/1980 | Luck et al. | 260/123.7 |
| 4,260,228 | 4/1981 | Miyata | 260/123.7 |
| 4,268,131 | 5/1981 | Miyata et al. | 530/356 |
| 4,505,855 | 3/1985 | Bruns et al. | 530/356 |

FOREIGN PATENT DOCUMENTS 28947 2/1980 Japan .................. 424/177

Primary Examiner—J. R. Brown
Assistant Examiner—Jacqueline M. Stone
Attorney, Agent, or Firm—Felfe & Lynch

[57] ABSTRACT

An improved, viscous, transparent, pyrogen-free, isotonic, succinylated atelocollagen solution provides an effective medium for use in viscosurgery and as a replacement for vitreous.

5 Claims, No Drawings

SUCCINYLATED ATELOCOLLAGEN SOLUTION FOR USE IN VISCOSURGERY AND AS A VITREOUS SUBSTITUTE

This application is a continuation, of application Ser. No. 693,084, filed Jan. 22, 1985, now abandoned.

According to the present invention improved viscous, transparent, pyrogen-free, isotonic solutions are prepared from succinylated collagen. The solutions are useful in viscosurgery and as a vitreous substitute.

According to one embodiment of the invention, an improved viscoelastic medium facilitates ophthalmic surgery procedures by preventing tissue damage, inter alia, as a result of its function as a lubricant. The medium also allows more room for surgical manipulation while insuring postoperative tissue separation which precludes adhesion formation. Ophthalmic surgery performed with the aid of such a viscoelastic medium is known in the art as viscosurgery.

According to another embodiment of the invention, the succinylated collagen solutions serve as an improved vitreous replacement suitable for intraocular implantation. The human vitreous humor is clear gel-like structure located in the posterior part of the eye. In cases of damaged vitreous, replacement of the damaged vitreous with a clear solution of succinylated collagen may aid in restoring sight.

BACKGROUND OF THE INVENTION

Prior to the present invention ophthalmic viscosurgery utilized solutions of fractionated sodium hyaluronate. The surgical uses of the latter composition are described in U.S. Pat. No. 4,141,973 (Balazs); in the article Pape, L. G., Balazs, E. A. "The Use of Sodium Hyaluronate (Healon) in Human Interior Segment Surgery" *Ophalmology* 87:699–705 (1980) and in the text *Healon (sodium hyaluronate) A Guide To its Uses In Ophthalamic Surgery,* D. Miller and R. Stigmann (John Wily & Sons). The succinylated collagen solutions of the present invention find utility in surgery as a replacement for such sodium hyaluronate solutions.

Succinylated collagen compositions are known and have been used in contact lenses, U.S. Pat. No. 4,223,984 (Miyata el al), in skin or wound dressings, U.S. Pat. No. 4,294,241 (Miyata), and in thin membranes suitable for ophthalmic drug delivery, U.S. Pat. No. 4,164,559 (Miyata et al). Stabilized collagen gels made from purified tropocollagen have been used as replacements for vitreous in rabbit and monkey eyes. Stenzel, K. H., Dunn, M. W., Rubin A. L. and Miyata, T. "Collagen Gels: Design for a Vitreous Replacement", *Science,* June 13, 1969 vol. 164 pp. 1282–1283. These unmodified collagen gels, however, proved deficient for they became opaque under pH conditions found within the eye.

DETAILED DESCRIPTION

Succinylated collagen for viscosurgery and vitreous replacement was prepared according to the following procedures:

EXAMPLE 1

Fresh calf skin was split into three layers, epidermal, corium and flesh. One kilogram of the corium layer was minced using a micro cutter and then washed with a 5% NaCl solution to remove soluble substances from the corium insoluble collagen. After washing with water, the minced corium collagen was treated with pepsin (pepsin: collagen=0.5:100 in weight) in 20 liters aqueous acidic solution (pH 3) at 20° C. for 3 days. During the pepsin treatment the mixture was slowly stirred. The corium insoluble collagen was completely solubilized by the pepsin treatment. Such pepsin treatment of collagen is preferred when preparing a biomaterial because the antigenic portion (telopeptides) of the collagen molecule are eliminated by pepsin treatment. The resulting collagen (atelocollagen) is superior for medical surgical uses to a collagen untreated with pepsin.

The solubilized pepsin-treated collagen solution was then filtered successively through 1.0, 0.6 and 0.45 u pore size membrane. The pH of the filtrate was adjusted to 7.5 and the reconstituted collagen fiber (atelocollagen) was collected by centrifuge. The atelocollagen fiber was redissolved in 5 liters of pH 3 aqueous solution and the pH was adjusted to 8 with NaOH solution. The atelocollagen which had dissolved in the acidic medium formed a precipitate when the pH was adjusted to 8 and a milky white atelocollagen suspension was obtained. To this suspension, 40 ml of acetone containing 4 g of succinic anhydride was gradually added under mixing at constant pH 8. To keep the pH 8 during addition of succinic anhydride, 1 N NaOH was gradually added. The reaction mixture was maintained at pH 8 under mixing overnight. During the succinylation reaction milky white atelocollagen precipitate was dissolved to a clear solution. After the reaction, the pH of the mixture was adjusted to 4.5 to form a precipitate of succinylated atelocollagen. The precipitate was collected by centrifuge and washed with water at pH 4.5, five (5) times to remove any unreacted succinic acid. The washed succinylated atelocollagen was freezed-dried for storage.

To make the final viscous succinylated atelocollagen solution useful for eye surgery, 10 g of freeze-dried succinylated atelocollagen was dissolved in 1 liter of phosphate buffered saline of pH 7.4 which contained 30 m mol $Na_2HPO_4$ and 200 m mol NaCl. The viscosity of the physiologic solution was 1200 centipoise (C.P.) and it was pyrogen-free.

When the sterile, pyrogen-free succinylated atelocollagen solution thus prepared was implanted into the anterior chamber of a rabbit eye, it showed minimal inflammatory reaction and remained clear, as is required for viscosurgery of the eye. This same viscous solution was used as a vitreous body substitute in a rabbit eye, and remained clear and showed minimal inflammatory reaction, demonstrating its utility as a vitreous substitute.

As will be appreciated by those skilled in the art, the viscosity of a succinylated atelocollagen solution can be controlled by adjusting the concentration of the atelocollagen, i.e., while a 1% solution has a viscosity of 1,200 C.P., a 2% solution has a viscosity of approximately 2,000 C.P. and a 3% solution has a viscosity of approximately 10,000 C.P. Useful buffered physiologic solutions will range from 0.5% to 5% by weight in concentration of atelocollagen.

Also, instead of sterilization of succinylated atelocollagen solution with 0.45 u millipore filtration, ethylene oxide gas (EOG) can be utilized. Freeze-dried succinylated atelocollagen may be conveniently treated with EOG and then dissolved in phosphate buffered saline after complete removal of excess EOG. Such an EOG sterilized succinylated atelocollagen solution is sterile, pyrogen-free, and useful as a viscosurgery material and as a vitreous body substitute.

The succinylation degree of the E-NH$_2$ group of atelocollagen can be controlled by controlling the amount of succinic anhydride, the pH and the time of reaction. The succinylation degree of the atelocollagen prepared by the method described above was over 85% and the isoelectric point of the atelocollagen was 4.5. The degree of succinylation can be determined by the TNBS (Trinitrogenen sulfuric acid) method (Kakade, M. L. and Liener, I. E. (1969) Anal. Biochem. 27, 273–280).

Atelocollagen which is succinylated to more than 10% of the total lysine residue (E-NH$_2$) is soluble at physiologic conditions (pH 7.0, isotonic condition). Therefore, for eye visco-surgery use, succinylation of more that 10% of the atelocollagen E-NH$_2$ groups is essential in order that the resulting solution be clear.

The denaturation temperature (TD) of succinylated atelocollagen is dependent on the succinylation degree. Since the TD drops with an increasing degree of succinylation, an upper limit on the desirable degree of succinylation is imposed. For example, the TD is 39.5° C. at 24% succinylation, 39.2° C. at 35% succinylation and 34.0° C. at 90% succinylation. A higher TD is of course, preferable for eye use. Therefore, while a 10% degree of succinylation of the E-NH$_2$ groups is necessary, a 20–50% succinylation degree is preferable.

EXAMPLE 2

Preparation of atelocollagen succinylated to varying degrees was accomplished as follows:

To 100 ml of 0.5% atelocollagen solution at pH 3.0 was added 0.1 N NaOH to adjust the pH to 9.0.

To this atelocollagen at pH 9.0, was added 0.1 ml of 1% succinic anhidride in acetone solution, and the pH of the reaction mixture was maintained at pH 9.0 by adding 0.1 N NaOH for 3 hours. Then the mixture was dialyzed against water to remove the succinic acid. The dialyzed succinylated atelocollagen was freeze-dried, and redissolved in physiologic saline, pH 7, at an atelocollagen concentration of 2%. The succinylation degree of this atelocollagen was 11.3%.

EXAMPLES 3 and 4

The above procedure was repeated using 0.3 ml and 1 ml of the 1% succinic anhydride acetone solution. The resulting atelocollagen samples had degrees of succinylation of 24% and 35% respectively.

We claim:

1. A solution of succinylated atelocollagen suitable for use in ophthalmic viscosurgery and vitreous replacement comprising atelocollagen succinylated to between about 10% to 50% of the total lysine residue and dissolved in a buffered solution to a concentration of between 0.5% and 5% by weight.

2. A solution for intraocular use, said solution comprising atelocollagen succinylated to between about 20% to 50% and dissolved in an aqueous buffer solution to a concentration of between about 0.5% and 5% by weight.

3. The solution of claim 1 wherein the atelocollagen is succinylated with succinic anhydride.

4. The solution of claim 3 wherein the aqueous buffer solution is phosphate buffered saline.

5. A solution of succinylated atelocollagen suitable for use in ophthalmic viscosurgery and vitreous replacement comprising atelocollagen succinylated to between about 10% to 50% of the total lysine residue and dissolved in a phosphate buffered saline solution of pH 7.0 to 7.4 to a concentration of between 0.5% and 5% by weight.

* * * * *